(12) United States Patent
Belt et al.

(10) Patent No.: US 9,610,384 B2
(45) Date of Patent: Apr. 4, 2017

(54) REDUCING THE DETERIORATON OF WETTED HYDROPHILIC COATINGS SUBJECTED TO STERILIZATION BY RADIATION

(71) Applicant: DSM IP ASSETS B.V., Heerlen (NL)

(72) Inventors: Johannes Wilhelmus Belt, Echt (NL); Robin Elisabeth Maria Jacobus Daenen, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/037,605

(22) PCT Filed: Nov. 20, 2014

(86) PCT No.: PCT/EP2014/075193
§ 371 (c)(1),
(2) Date: May 18, 2016

(87) PCT Pub. No.: WO2015/075141
PCT Pub. Date: May 28, 2015

(65) Prior Publication Data
US 2016/0288940 A1   Oct. 6, 2016

(30) Foreign Application Priority Data

Nov. 20, 2013   (EP) .................................... 13193707
Nov. 20, 2013   (EP) .................................... 13193715

(51) Int. Cl.
| | | |
|---|---|---|
| *C08J 7/18* | (2006.01) | |
| *A61L 29/08* | (2006.01) | |
| *A61L 29/14* | (2006.01) | |
| *A61L 31/10* | (2006.01) | |
| *A61L 31/14* | (2006.01) | |
| *A61L 2/08* | (2006.01) | |
| *A61L 29/04* | (2006.01) | |
| *B65B 55/08* | (2006.01) | |
| *B65B 55/16* | (2006.01) | |
| *B65D 81/20* | (2006.01) | |
| *A61B 50/30* | (2016.01) | |
| *B65D 81/26* | (2006.01) | |

(52) U.S. Cl.
CPC ............ *A61L 29/085* (2013.01); *A61B 50/30* (2016.02); *A61L 2/081* (2013.01); *A61L 2/087* (2013.01); *A61L 29/041* (2013.01); *A61L 29/14* (2013.01); *A61L 29/143* (2013.01); *A61L 31/10* (2013.01); *A61L 31/14* (2013.01); *A61L 31/143* (2013.01); *B65B 55/08* (2013.01); *B65B 55/16* (2013.01); *B65D 81/2069* (2013.01); *B65D 81/266* (2013.01); *A61L 2300/428* (2013.01); *A61L 2400/10* (2013.01); *A61L 2420/02* (2013.01); *A61L 2420/06* (2013.01)

(58) Field of Classification Search
USPC ............... 205/210, 220, 353, 355, 361, 471; 606/70, 151, 280
See application file for complete search history.

(56) References Cited

U.S. PATENT DOCUMENTS

| | | |
|---|---|---|
| 2003/0224033 A1 | 12/2003 | Li et al. |
| 2008/0044643 A1* | 2/2008 | Yokota ................. B01D 63/021 428/308.4 |
| 2009/0246253 A1 | 10/2009 | Ding |
| 2011/0058982 A1 | 3/2011 | Kaneko |
| 2011/0106061 A1 | 5/2011 | Nielsen et al. |
| 2011/0212152 A1 | 9/2011 | Ditizio et al. |
| 2013/0131701 A1 | 5/2013 | Komlos et al. |
| 2016/0287757 A1* | 10/2016 | Belt ...................... A61L 29/085 |

FOREIGN PATENT DOCUMENTS

| | | |
|---|---|---|
| WO | WO 2007137699 | 12/2007 |
| WO | WO 2011076217 | 6/2011 |

OTHER PUBLICATIONS

ISA Report.
Written Opinion.
William A. Pryor, The Kinectics of the Disproportion of Sodium Thiosulfate to Sodium Sulfide and Sulfate, Contribution from the California Research Corp, Richmond, CA, Feb. 17, 1960, pp. 4794-4797, vol. 82.

\* cited by examiner

*Primary Examiner* — Bernard Souw
(74) *Attorney, Agent, or Firm* — Kevin M. Bull

(57) ABSTRACT

A method of reducing the deterioration of a wetted hydrophilic coating caused by sterilization by radiation is provided. The method comprises the step of incorporating a thiosulfate anion and a buffer into the wetting hydrophilic coating comprising water. Some embodiments of the invention relate to a wetted hydrophilic coating, a wetting agent, a package comprising a wetted hydrophilic coating, and a method of sterilizing a wetted hydrophilic coating.

20 Claims, No Drawings

REDUCING THE DETERIORATON OF WETTED HYDROPHILIC COATINGS SUBJECTED TO STERILIZATION BY RADIATION

This application is the U.S. national phase of International Application No. PCT/EP2014/075193, filed 20 Nov. 2014, which designated the US and claims priority to European Application Nos. EP13193707.0 and EP13193715.3, both filed 20 Nov. 2013, the entire contents of each of which are hereby incorporated by reference.

FIELD OF THE INVENTION

The field of the invention is the sterilization and stabilization of wetted hydrophilic coatings.

BACKGROUND OF THE INVENTION

Many medical devices, such as guide wires, intermittent and (cardio)vascular catheters or other medical tubing, syringes, and membranes require some sort of lubrication in order to facilitate insertion into or removal from the body. Pain or soft tissue damage can occur upon insertion or removal of the medical device if the medical device is not properly lubricated.

Many medical devices are coated with a hydrophilic coating that must be wetted with a liquid to attain the sufficient level of lubrication. A hydrophilic coating is typically provided as a coating on a surface of a medical device. The act of wetting a hydrophilic coating is performed by causing the hydrophilic coating to retain a wetting agent. Upon being wetted with a wetting agent, a hydrophilic coating may absorb at least two times its weight of the wetting agent and be rendered lubricious. A hydrophilic coating that does not absorb at least two times its weight of wetting agent will likely be insufficiently lubricous. The wetting agent may be any number of water or oil-based products, for example those disclosed in WO2006037321, assigned to Coloplast A/S, or WO2013017547, assigned to DSM IP Assets B.V.

Water-based wetting agents are often preferred by users. Unlike oil-based wetting agents, such as those that contain more than 50% by weight of propylene glycol or glycerol, water-based wetting agents do not have the disadvantage of leaving an oily residue on surfaces that come in contact with the wetted hydrophilic coating, such as a user's fingers. Furthermore, although a hydrophilic coating that is wetted with an oil-based wetting agent generally has good lubricious properties and dry-out time, improved lubricity can often be realized when a hydrophilic coating is wetted with a water-based wetting agent. Dry-out time is the amount of time that the wetted hydrophilic coating can retain suitable lubricious properties.

A hydrophilic coating may be wetted in a number of ways, depending on the composition of the wetting agent and the medical device design. For example, the hydrophilic coating may be wetted by submersing the hydrophilic coating in the wetting agent, spraying the wetting agent on the hydrophilic coating, running wetting agent over the hydrophilic coating for a short period of time, injecting the wetting agent into a packaging containing an article comprising a hydrophilic coating, or applying the wetting agent to the hydrophilic coating in the form of a gas, for instance in a high humidity environment.

The hydrophilic coating may be wetted immediately prior to use. Wetting immediately prior to use requires access to a wetting agent, for instance, a water source. Moreover, wetting immediately prior to use requires handling of the medical device at the risk of contacting the medical device with bacteria.

Because of the disadvantages with wetting the hydrophilic coating on a medical device immediately prior to use, numerous medical devices have been introduced that are sterile, pre-wetted, and individually packaged for immediate use. The use of so-called "ready-to-use" products may reduce the risk of contact with bacteria, and allows for the medical device to be used when access to a wetting agent is not practical or possible. A ready-to-use product typically comprises a wetted hydrophilic coating wherein the wetted hydrophilic coating comprises at least 70 wt %, or more preferably at least 90 wt % of wetting agent, based on the total weight of the wetted hydrophilic coating (i.e. the combined weight of the wetting agent and the hydrophilic coating). A product that does not possess a wetted hydrophilic coating that is sufficiently lubricious is not a ready-to-use product. An example of a ready-to-use product is described in U.S. Pat. No. 7,380,658, hereby incorporated by reference in its entirety.

In addition to numerous benefits, ready-to-use products present numerous challenges. One challenge faced is to avoid a reduction in the lubricious properties, durability, or dry-out time of the hydrophilic coating after sterilization. Certain sterilization techniques, such as sterilization with radiation, are known to potentially degrade the beneficial properties of a wetted hydrophilic coating. Consequently, various attempts have been made to reduce the damaging effects of sterilization on the beneficial properties of a hydrophilic coating wetted with a wetting agent comprising water prior to sterilization.

For example, a known technique described in WO/2000/030696, assigned to Coloplast A/S, involves wetting a hydrophilic coating on a medical device with an aqueous wetting agent comprising a hydrophilic polymer prior to sterilizing the medical device. However, the presence of polymers in the water phase can leave sticky residues on fingers and clothes. Moreover, an insufficiently cross-linked additional coating layer may be formed that is not acceptably durable. A similar technique disclosed in US2011/0106061, assigned to Coloplast A/S, suffers from similar disadvantages. This technique mentions a medical device comprising a hydrophilic coating, sterilized while in contact with a liquid comprising a hydrophilic polymer and a separate buffer selected from the group consisting of carboxylic acids, amino acids, aminosulphonic acids and inorganic acids.

Another known technique described in WO/2007/137699, assigned to DSM IP Assets B.V., involves the use of a compound selected from the group consisting of aliphatic compounds, alicyclic compounds and antioxidants for protecting a hydrophilic coating wetted with water. This technique may provide insufficient protection from the damaging effects of radiation at certain doses of radiation, such as greater than 30 kGy.

A further technique is disclosed in US2014/0271351, assigned to Coloplast A/S. This technique discloses a medical device comprising a hydrophilic coating, sterilized while in contact with a swelling medium comprising a low molecular polyol; and a separate buffer selected from the group consisting of carboxylic acids, amino acids, aminosulphonic acids and inorganic acids. The swelling media allegedly provides a stable pH after sterilization and maintains the low friction of the wetted hydrophilic coating.

An improved way of protecting a hydrophilic coating wetted with a wetting agent comprising water prior to sterilization from the damaging effects of radiation is desired.

SUMMARY

In accordance with the invention, the deterioration of a wetted hydrophilic coating comprising water and subjected to sterilization by radiation is reduced by incorporating a thiosulfate anion and a buffer for maintaining the pH at 6 or above, more preferably at 6.5 or above, more preferably at 7 or above in the wetted hydrophilic coating. In another embodiment, a wetting agent for wetting a hydrophilic coating comprises water, a thiosulfate anion, and a buffer for maintaining the pH at 6 or above, more preferably at 6.5 or above, more preferably at 7 or above.

Further embodiments of the invention relate to a method of sterilizing a packaged article comprising the step of sterilizing with radiation a package comprising an article and a gas impermeable packaging enclosing the article, the article comprising a wetted hydrophilic coating and the wetted hydrophilic coating comprising water, a thiosulfate anion, and a buffer for maintaining the pH at 6 or above, more preferably at 6.5 or above, more preferably at 7 or above.

A further embodiment of the invention relates to a method of packaging an article comprising forming a wetted hydrophilic coating comprising water, a thiosulfate anion, and a buffer for maintaining the pH at 6 or above, more preferably at 6.5 or above, more preferably at 7 or above, on an article, and enclosing the article in a gas impermeable packaging.

Another embodiment of the invention is a package comprising an article, the article comprising a wetted hydrophilic coating, the wetted hydrophilic coating comprising water, a thiosulfate anion, and a buffer for maintaining the pH at 6 or above, more preferably at 6.5 or above, more preferably at 7 or above, and a gas impermeable packaging enclosing the article. The package is preferably sterilized.

In such embodiments, the article is preferably a medical device, such as a catheter, guidewire, syringe, or contact lens.

Further embodiments of the invention are elucidated in the following detailed description.

DETAILED DESCRIPTION

As mentioned above, the prior art of reducing the deterioration of wetted hydrophilic coatings subject to sterilization by radiation has not sufficiently provided a solution, especially when the wetting agent comprises water.

The prior art has recognized some reduction in deterioration may occur from employing components that may have oxygen and radical scavenging capabilities in the wetted hydrophilic coating, but a sufficient level of deterioration reduction was not obtained. For example, WO/2007/137699 mentions Vitamin C, which may act as both an oxygen scavenger and a radical scavenger. However, WO/2007/137699 notes that when a hydrophilic coating wetted with a wetting agent consisting essentially of water and Vitamin C is sterilized with 25 kGy of gamma radiation, as shown in Examples B and C of WO/2007/137699, "some improvement was observed compared to sterilization in pure water, but . . . a desirable dry-out time was not realized." Additionally, the improvement exhibited with a wetting agent consisting essentially of water and 2 wt % vitamin C exhibited coloration after sterilization.

In accordance with the invention, the deterioration of a wetted hydrophilic coating comprising water and subjected to sterilization by radiation is reduced by incorporating a thiosulfate anion and a buffer for maintaining the pH at 6 or above, more preferably at 6.5 or above, more preferably at 7 or above in the wetted hydrophilic coating.

A hydrophilic coating is typically provided on a surface of an article. A hydrophilic coating may be provided in a number of ways, such as extrusion, molding, or curing. In the case of curing, a hydrophilic coating composition is cured to form a hydrophilic coating. Radiation curing may be performed by curing with heat and/or light, such as UV light. Preferably, the hydrophilic coating is formed by curing a hydrophilic coating composition by radiation comprising UV light.

A typical hydrophilic coating may be obtained by providing on a surface of an article, said surface may or may not being already primed by a primer, a hydrophilic coating composition and curing the hydrophilic coating composition. A typical hydrophilic coating composition comprises a hydrophilic polymer, a solvent, and an initiator. Examples of hydrophilic polymers are polyvinylpyrrolidone (PVP), polyacrylamide, polyelectrolytes, and poly(ethylene oxide). Hydrophilic polymers may also comprise reactive groups, such as (meth)acrylate groups) or photo-active groups, in addition to a hydrophilic portion. The initiator is typically a photoinitiator. One or more supporting monomers, oligomers, or polymers having reactive moieties to support the hydrophilic polymer or other components or additives, such as plasticizers or surfactants, may also be present. A solvent may be, for example, water, methanol or ethanol. The hydrophilic coating may be obtained by at least partially evaporating the solvent from the hydrophilic coating composition and then curing the hydrophilic coating composition with light, such as UV light. Hydrophilic coating compositions are disclosed in, for example, US2011046255 to DSM IP Assets BV, which is hereby incorporated by reference in its entirety. A commercial example of a hydrophilic coating composition that may be cured by radiation comprising UV light to form a hydrophilic coating is a ComfortCoat® product from DSM, such as TC43005.

A primer may be present to improve the adherence of the hydrophilic coating to an article. The primer may be cured prior to application and curing of a hydrophilic coating composition, or may be cured at the same time as the hydrophilic coating composition is cured.

A typical primer composition may comprise a supporting monomer, oligomer, or polymer that provides the necessary adherence to the article, an initiator, and a solvent. The initiator is typically a photoinitiator. A hydrophilic polymer, such as polyvinylpyrrolidone (PVP) and poly(ethylene oxide), may also be present. The primer may be formed by at least partially evaporating the solvent from the primer composition and then curing the primer composition with UV light. Subsequently, a hydrophilic coating composition may be applied on top of the primer and cured to form a hydrophilic coating.

In an embodiment, a hydrophilic coating is formed by curing a hydrophilic coating composition, the hydrophilic coating composition comprising at least 70 wt %, preferably at least 80 wt %, more preferably at least 90 wt % of hydrophilic polymer, based on the total dry weight of the hydrophilic coating composition. By dry weight it is meant the total weight of the hydrophilic coating composition excluding any solvents.

A wetted hydrophilic coating may be formed in a number of ways. The process of forming a wetted hydrophilic coating from a hydrophilic coating is known as wetting the hydrophilic coating. Wetting can be accomplished by, for example, bringing a wetting agent present as a liquid into contact with a hydrophilic coating. The contact may be established in a number of ways, for instance, submerging the hydrophilic coating in the wetting agent or spraying the hydrophilic coating with the wetting agent. Other methods of wetting a hydrophilic coating may be performed with a wetting agent present as a gas or vapor. For instance, a liquid wetting agent may be present out of direct contact with the hydrophilic coating, but the wetting agent wets the hydrophilic coating by traveling as a gas or vapor. Similarly, a high humidity environment could be present in a package containing an article comprising a hydrophilic coating such that over time the hydrophilic coating is wetted. In a wetting method where the wetting agent wets the hydrophilic coating as a gas or vapor, components that may normally be included in the wetting agent that cannot travel as a vapor or gas would need to be incorporated into the wetted hydrophilic coating by other means, such as inclusion in the hydrophilic coating itself. The thickness of a typical wetted hydrophilic coating is generally more than 0.5 micron and less than 100 microns.

Sterilization is typically performed by radiation. Methods of sterilization by radiation include sterilization by gamma rays, x-rays, and electron beams. In the medical device area, gamma ray or electron beam sterilization are generally preferred. In an embodiment, sterilization is performed by gamma rays or electron beam. In an embodiment, sterilization is performed by gamma rays or electron beam at a dosage of greater than 25 kGy, preferably greater than 30 kGy. Catheters are typically sterilized with a dose of radiation of from 25 to 50 kGy, preferably 25 to 45 kGy.

Generally, chemical or other means of sterilization present difficulties when sterilizing wetted hydrophilic coatings. Chemical sterilization, such as sterilization with ethylene oxide, requires the use of a gas that must contact the article that is being sterilized. A vacuum is then applied to remove the gas. This vacuum may adversely affect the wetted hydrophilic coating by removing some of the liquid components of a wetting agent retained by the wetted hydrophilic coating, thereby reducing the lubricity of the wetted hydrophilic coating. Moreover, depending on the type of packaging used, a chemical sterilization may not fully penetrate a sealed package and consequently not sufficiently sterilize the article.

In accordance with the invention, a thiosulfate anion is incorporated into the wetted hydrophilic coating. The thiosulfate anion is represented by the chemical formula $S_2O_3^{2-}$. Compounds comprising thiosulfate anions are, for example, sodium thiosulfate, ammonium thiosulfate, barium thiosulfate, calcium thiosulfate, magnesium thiosulfate, potassium thiosulfate or hydrates thereof. Additional compounds comprising a thiosulfate anion are lithium thiosulfate, iron thiosulfate, zinc thiosulfate, tin thiosulfate, silver thiosulfate or hydrates thereof. In an embodiment, a thiosulfate anion is incorporated in the wetted hydrophilic coating by incorporating a compound selected from the group consisting of sodium thiosulfate, ammonium thiosulfate, barium thiosulfate, calcium thiosulfate, magnesium thiosulfate, potassium thiosulfate and hydrates thereof. In an embodiment, a thiosulfate anion is incorporated in the wetted hydrophilic coating by incorporating a compound selected from the group consisting of lithium thiosulfate, iron thiosulfate, zinc thiosulfate, tin thiosulfate, silver thiosulfate or hydrates thereof. In another embodiment, a thiosulfate anion is incorporated in the wetted hydrophilic coating by wetting a hydrophilic coating with a wetting agent comprising a compound selected from the group consisting of sodium thiosulfate, ammonium thiosulfate, barium thiosulfate, calcium thiosulfate, magnesium thiosulfate, potassium thiosulfate and hydrates thereof. In another embodiment, a thiosulfate anion is incorporated in the wetted hydrophilic coating by wetting a hydrophilic coating with a wetting agent comprising a compound selected from the group consisting of lithium thiosulfate, iron thiosulfate, zinc thiosulfate, tin thiosulfate, silver thiosulfate or hydrates thereof.

The thiosulfate anion is typically present in a wetting agent for wetting a hydrophilic coating in an amount of 0.05 to 3 wt %, based on the total weight of the wetting agent, more preferably from 0.1 to 2.5 wt %, more preferably from 0.3 to 2.0 wt %, even more preferably from 0.3 to 1.5 wt %, based on the total weight of the wetting agent. In an embodiment, the thiosulfate anion is present at an amount of from 0.5 to 2.0 wt %, more preferably from 0.5 to 1.5 wt %, based on the total weight of the wetting agent.

The stability of the wetted hydrophilic coating in a ready-to-use product is important. Typically, ready-to-use catheter products are prescribed a three year shelf life. Normally a hydrophilic coating that is not wetted does not have the stability problems observed in a wetted hydrophilic coating. A buildup of a foul smell in the product packaging may occur over the period of storage if there is instability in the wetted hydrophilic coating. The instability may come from the hydrophilic coating, the wetting agent, or a combination of the two. It is suspected that the observed instability may be associated with any deterioration reduction mechanism, such as a thiosulfate anion, that may be incorporated into the wetted hydrophilic coating. The instability may be caused by either pre-sterilization instability (i.e. the wetted hydrophilic coating is unstable at the time of sterilization) or post-sterilization instability.

In an embodiment, the pH of the wetted hydrophilic coating or the wetting agent is from 6 to 9, more preferably from 6.5 to 9, more preferably from 6.5 to 8.5, more preferably from 7 to 8, more preferably from 7 to 7.5. In an embodiment, the pH of a wetting agent for wetting a hydrophilic coating is from 6 to 9, more preferably from 6.5 to 9, more preferably from 6.5 to 8.5, more preferably from 7 to 8, more preferably from 7 to 7.5. In an embodiment, the pH of the wetted hydrophilic coating or the wetting agent is from 7 to 9, more preferably from 7 to 8.5, more preferably from 7 to 8. In an embodiment, the pH of a wetting agent for wetting a hydrophilic coating is from 7 to 9, 7 to 8.5, more preferably from 7 to 8.

To maintain stability of a wetted hydrophilic coating or wetting agent comprising a thiosulfate anion, it is preferred that the wetted hydrophilic coating or wetting agent is maintained at a pH of 6 or higher, more preferably 6.5 or higher, more preferably 7 or higher. The wetted hydrophilic coating or wetting agent comprises a buffer to render the wetted hydrophilic coating or wetting agent resistant to changes in pH. In an embodiment, a wetted hydrophilic coating comprises a thiosulfate anion, water, and a buffer for maintaining the pH at 6 or above, more preferably at 7 or above. In an embodiment, a wetting agent for wetting a hydrophilic coating comprises a thiosulfate anion, water, and a buffer for maintaining the pH at 6 or above, more preferably at 7 or above. In an embodiment, a wetting agent for wetting a hydrophilic coating comprises a thiosulfate anion, water, and a buffer for maintaining the pH at 6.5 or above, more preferably at 7 or above. In an embodiment, a wetted hydrophilic coating comprises a thiosulfate anion, water, and a buffer for maintaining the pH at 6.5 or above, more preferably at 7 or above. In an embodiment, a wetted hydrophilic coating comprises a thiosulfate anion, water, and a buffer for maintaining the pH at from 6 to 9, more preferably from 6.5 to 9, more preferably from 7 to 9, more preferably from 7 to 8.5. In an embodiment, a wetting agent for wetting a hydrophilic coating comprises a thiosulfate anion, water, and a buffer for maintaining the pH at from 6 to 9, more preferably from 6.5 to 9, more preferably from 7 to 9, more preferably from 7 to 8.5.

In an embodiment, the buffer comprises a base. Suitable bases are water soluble compounds with a pKb between 1 and 15, more preferably from 5 to 10. Examples of suitable bases are sodium carbonate, sodium acetate, sodium formate, and sodium benzoate. In an embodiment, a wetted hydrophilic coating comprises a thiosulfate anion, water, and a buffer for maintaining the pH at 6 or above, more preferably at 7 or above, wherein the buffer comprises a base. In an embodiment, a wetting agent for wetting a hydrophilic coating comprises a thiosulfate anion, water, and a buffer for maintaining the pH at 6 or above, more preferably at 7 or above, wherein the buffer comprises a base. In an embodiment, a wetting agent for wetting a hydrophilic coating comprises a thiosulfate anion, water, and a buffer for maintaining the pH at 6.5 or above, more preferably at 7 or above, wherein the buffer comprises a base. In an embodiment, a wetted hydrophilic coating comprises a thiosulfate anion, water, and a buffer for maintaining the pH at 6.5 or above, more preferably at 7 or above, wherein the buffer comprises a base. In an embodiment, a wetted hydrophilic coating comprises a thiosulfate anion, water, and a buffer for maintaining the pH at from 6 to 9, more preferably from 6.5 to 9, more preferably from 7 to 9, more preferably from 7 to 8.5, wherein the buffer comprises a base. In an embodiment, a wetting agent for wetting a hydrophilic coating comprises a thiosulfate anion, water, and a buffer for maintaining the pH at from 6 to 9, more preferably from 6.5 to 9, more preferably from 7 to 9, more preferably from 7 to 8.5, wherein the buffer comprises a base.

Suitable buffers may comprise a phosphate buffer, ACES, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, AMPSO, salts of any of the foregoing, and combinations of any of the foregoing. Preferably, the buffer comprises a phosphate buffer. In an embodiment, the phosphate buffer comprises phosphate monobasic and phosphate dibasic. In an embodiment, the phosphate buffer comprises a salt and/or hydrate of phosphate monobasic and a salt and/or hydrate of phosphate dibasic. In an embodiment, the buffer comprises sodium phosphate monobasic monohydrate and sodium phosphate dibasic heptahydrate.

The buffer capacity is the number of moles of strong acid or strong base that, when added to 1 liter of buffer solution, changes its pH by 1 unit. The buffer capacity can be calculated using the equation:

$$\beta = 2.303 \times C \times \frac{Ka \times [H_3O^+]}{(Ka + [H_3O^+])^2}$$

where β is the buffer capacity, 2.303 is a constant, C is the molar concentration of the buffer, Ka is the acid ionization constant and $[H_3O^+]$ is the concentration of $H_3O^+$.

In an embodiment, the buffer capacity is 5 mmol or greater at at least one starting pH of from 6 to 8.5. In an embodiment, the buffer capacity is 5 mmol or greater at at least one starting pH of from 6 to 8. In an embodiment, the buffer capacity is 5 mmol or greater at at least one starting pH of from 6.5 to 8. In an embodiment, the buffer capacity is 5 mmol or greater at at least one starting pH of from 7 to 8. In an embodiment, the buffer capacity is from 5 mmol to 500 mmol at at least one starting pH of from 6 to 8.5. In an embodiment, the buffer capacity is from 5 mmol to 500 mmol at at least one starting pH of from 6 to 8. In an embodiment, the buffer capacity is from 5 mmol to 500 mmol at at least one starting pH of from 6.5 to 8. In an embodiment, the buffer capacity is from 5 mmol to 500 mmol at at least one starting pH of from 7 to 8. In an embodiment, the buffer capacity is from 5 mmol to 300 mmol at at least one starting pH of from 6 to 8.5. In an embodiment, the buffer capacity is from 5 mmol to 300 mmol at at least one starting pH of from 6 to 8. In an embodiment, the buffer capacity is from 5 mmol to 300 mmol at at least one starting pH of from 6.5 to 8. In an embodiment, the buffer capacity is from 5 mmol to 300 mmol at at least one starting pH of from 7 to 8.

In further embodiments, preservatives are present in the wetted hydrophilic coating or wetting agent to prevent microbial growth prior to sterilization. Examples of preservatives are methyl paraben, ethyl paraben, propyl paraben, salts of sulfite such as sodium sulfite, sorbic acid, calcium propionate, benzoic acid, salts of hydrosulfite such as sodium hydrogen sulfite, sodium bisulfite, sodium benzoate, erythorbic acid, and salts of nitrate such as potassium nitrate.

In accordance with the invention, the wetted hydrophilic coating comprises water. In embodiments, the wetted hydrophilic coating comprises at least 50 wt %, more preferably at least 70 wt %, or more preferably at least 90 wt % water, based on the total weight of the wetted hydrophilic coating. In embodiments wherein the wetted hydrophilic coating is wetted with a wetting agent further comprising water, the amount of water in the wetting agent is preferably 50 wt % or more. In embodiments, the amount of water in the wetting agent is 80 wt % or more, and in further embodiments at least 90 wt % or more. In an embodiment, a wetting agent further comprises at least 95 wt % water.

In an embodiment, a wetting agent for wetting a hydrophilic coating consists essentially of water, a thiosulfate anion, and a buffer for maintaining the pH at 6 or above, more preferably at 6.5 or above, more preferably at 7 or above. Preservatives or other components that do not materially affect the basic and novel properties of the invention may be present. In an embodiment, a wetting agent for wetting a hydrophilic coating consists essentially of at least 90 wt % of water, from 0.1 to 2.5 wt % of a thiosulfate anion, both based on the total weight of the wetting agent, and a buffer for maintaining the pH at 6 or above, more preferably at 6.5 or above, more preferably at 7 or above. In an embodiment, a wetting agent for wetting a hydrophilic coating consists essentially of at least 95 wt % of water, from 0.3 to 2 wt % of a thiosulfate anion, both based on the total weight of the wetting agent, and a buffer for maintaining the pH at 6 or above, more preferably at 6.5 or above, more preferably at 7 or above. In an embodiment, a wetting agent for wetting a hydrophilic coating consists essentially of at least 95 wt % of water, from 0.5 to 2 wt % of a thiosulfate anion, both based on the total weight of the wetting agent, and a buffer for maintaining the pH at 6 or above, more preferably at 6.5 or above, more preferably at 7 or above.

In an embodiment of the invention, a wetting agent for wetting a hydrophilic coating comprises water, a thiosulfate anion, a buffer for maintaining the pH at 6 or above, more preferably at 6.5 or above, more preferably at 7 or above, and a preservative. In an embodiment, a wetting agent for wetting a hydrophilic coating comprises at least 90 wt % of water, from 0.05 to 3 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 90 wt % of water, from 0.1 to 2.5 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 90 wt % water, from 0.3 to 1.5 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 90 wt % water, from 0.5 to 1.5 wt % of a thiosulfate anion, a buffer for maintaining the pH at 6 or above, more preferably at 6.5 or above, more preferably at 7 or above, and a preservative, based on the total weight of the wetting agent. In an embodiment, a wetting agent for wetting a hydrophilic coating comprises at least 95 wt % of water, from 0.05 to 3 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 95 wt % of water, from 0.1 to 2.5 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 95 wt % water, from 0.3 to 1.5 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 95 wt % water, from 0.5 to 1.5 wt % of a thiosulfate anion, a buffer for maintaining the pH at 6 or above, more preferably at 6.5 or above, more preferably at 7 or above, and a preservative, based on the total weight of the wetting agent. In an embodiment, a wetting agent for wetting a hydrophilic coating comprises at least 97 wt % of water, from 0.05 to 3 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 97 wt % of water, from 0.1 to 2.5 wt % of a thiosulfate anion, a buffer for maintaining the pH at 6 or above, more preferably at 6.5 or above, more preferably at 7 or above, and a preservative, based on the total weight of the wetting agent. In another embodiment, a wetting agent for wetting a hydrophilic coating comprises at least 97 wt % water, from 0.3 to 1.5 wt % of a thiosulfate anion, a buffer and a preservative, based on the total weight of the wetting agent. In another embodiment, a wetting agent for wetting a hydrophilic coating comprises at least 97 wt % water, from 0.5 to 1.5 wt % of a thiosulfate anion, a buffer for maintaining the pH at 6 or above, more preferably at 6.5 or above, more preferably at 7 or above, and a preservative, based on the total weight of the wetting agent.

In an embodiment, a wetting agent for wetting a hydrophilic coating consists essentially of water, a thiosulfate anion, a buffer for maintaining the pH at 6 or above, more preferably at 6.5 or above, more preferably at 7 or above, and a preservative. In an embodiment, a wetting agent for wetting a hydrophilic coating consists essentially of at least 97 wt % of water, from 0.1 to 2.5 wt % of a thiosulfate anion, a buffer for maintaining the pH at 6 or above, more preferably at 6.5 or above, more preferably at 7 or above, and a preservative, based on the total weight of the wetting agent. In an embodiment, a wetting agent for wetting a hydrophilic coating consists essentially of at least 98 wt % of water, from 0.3 to 1.5 wt % of a thiosulfate anion, a buffer for maintaining the pH at 6 or above, more preferably at 6.5 or above, more preferably at 7 or above, and a preservative, based on the total weight of the wetting agent. In an embodiment, a wetting agent for wetting a hydrophilic coating consists essentially of at least 98 wt % of water, from 0.5 to 1.5 wt % of a thiosulfate anion, a buffer for maintaining the pH at 6 or above, more preferably at 6.5 or above, more preferably at 7 or above, and a preservative, based on the total weight of the wetting agent.

In a further embodiment, a further scavenger is incorporated into the wetted hydrophilic coating. The further scavenger may be a further radical scavenger and/or a further oxygen scavenger. Some benefit may be obtained from including a further scavenger depending on the type of wetted hydrophilic coating or sterilization. Potentially lesser amounts of components serving as oxygen scavengers and/or radical scavengers are needed in a wetted hydrophilic coating comprising a thiosulfate anion than would normally be present in a wetted hydrophilic coating without a thiosulfate anion. This provides the advantage of allowing for components, such as additional water, that perform the sole function of providing lubricity to the wetted hydrophilic coating or have a lower raw material cost.

In the case that the wetted hydrophilic coating will be inserted into the body, for instance in the case of a catheter, any further scavenger should be biocompatible. Biocompatible means that a material has the ability to be in contact with a living system without producing an adverse effect.

In embodiments of the invention, the further scavenger is a further radical scavenger. In principle any known radical scavenger that is soluble in water could be used. In an embodiment where a further radical scavenger is present in a wetted hydrophilic coating, the total concentration of further radical scavenger in the wetting hydrophilic coating is preferably from 0.01 to 2 wt %, based on the total weight of wetted hydrophilic coating. In the case that a further radical scavenger is present in a wetting agent for wetting a hydrophilic coating, the total concentration of further radical scavenger in the wetting agent is from 0.01 to 2 wt %, based on the total weight of wetting agent.

Preferably, the further radical scavenger is also a further oxygen scavenger. In an embodiment, a wetted hydrophilic coating and/or a wetting agent further comprises a further radical scavenger and a further oxygen scavenger. Preferably, the further radical scavenger and further oxygen scavenger is vitamin c (ascorbic acid). In the case that the further radical scavenger is also a further oxygen scavenger and is present in a wetting agent for wetting a hydrophilic coating, the total concentration of further radical scavenger that is also an oxygen scavenger in the wetting agent is from 0.01 to 1 wt % based on the total weight of wetting agent, more preferably 0.05 to 1 wt % based on the total weight of wetting agent.

Suitable compounds that are radical scavengers but not oxygen scavengers are, for example, alkyl hydroxybenzyl alcohols (such as 5-di-tert-butyl-4-hydroxybenzyl alcohol), alkyl hydroxybenzoic acids (such as 3,5-di-tert-butyl-4-hydroxybenzoic acid), pyrogallol, alkylated hydroxytoluene (such as butylated hydroxy toluene), and 2,6-ditertbutyl-4-ethyl-phenol. Commercially available examples of such radical scavengers that are not oxygen scavengers include Irganox® 1300, Irganox® 1098, Irganox® 1076 and combinations thereof. If present, a compound that is a radical scavenger but not an oxygen scavenger may be present in an amount of from 0.05 to 1 wt %, based on the total weight of wetting agent.

The thiosulfate anion and the further scavenger may be incorporated into the wetted hydrophilic coating in a number of ways. For example, as part of a wetting agent that is used to wet the hydrophilic coating, as part of the hydrophilic coating, or as part of both the wetting agent and the hydrophilic coating. If present in the wetting agent, the component may be incorporated in the wetting agent by simple mixing. If present in the hydrophilic coating, the component may be incorporated in the hydrophilic coating composition.

In an embodiment, a further water soluble organic component and/or water soluble polymer is incorporated into the wetted hydrophilic coating or present in a wetting agent. Such components may be, for example, polyvinylpyrrolidone, acrylic acid or acrylic acid copolymers, polyacrylamides, polyethylene glycol, and/or polyelectrolytes such as salts of (meth)acrylic acid copolymers, for example, poly(acrylamide-co-acrylic acid) salt.

Further alcohols may be present in the wetted hydrophilic coating and/or wetting agent in limited amounts. In an embodiment, the wetted hydrophilic coating and/or wetting agent comprises a component selected from the group consisting of glycerol, glycerol esters, glycerol ethers, glycols, glycolesters and glycolethers. Suitable examples of components are glycerol, monoacetin, diacetin, diacetone alcohol, diethyleneglycol, triethyleneglycol, tetraethyleneglycol, propyleneglycol or dipropyleneglycol. If present, it is preferred that such components are present at from 1 wt % to 20 wt %, more preferably from 2 wt % to 10 wt %, more preferably from 4 wt % to 10 wt %, based on the total weight of the wetting agent.

In embodiments of the invention, further components that may be present in the wetted hydrophilic coating and/or wetting agent are additional preservatives, surfactants, antibiotics, and/or anti-microbial compounds.

In an embodiment, the amount of oxygen in an atmosphere in contact with the wetted hydrophilic coating is reduced in addition to any reduction in oxygen provided by oxygen scavengers that may be present in the wetted hydrophilic coating. The atmosphere in contact with the wetted hydrophilic coating means the gas surrounding and in contact with the wetted hydrophilic coating at the time of sterilization. For example, the atmosphere may be contained within a gas impermeable package or within a sterilization apparatus.

An oxygen scavenger present in the wetted hydrophilic coating will, depending on type and amount, generally provide some reduction in the oxygen in the atmosphere in contact with the wetted hydrophilic coating. However, deterioration of the wetted hydrophilic coating may be improved in certain circumstances by a further reduction in the amount of oxygen in the atmosphere in contact with the wetted hydrophilic coating in addition to any reduction in oxygen provided by oxygen scavengers that may be present in the wetted hydrophilic coating. In an embodiment, the amount of oxygen in the atmosphere in contact with the wetted hydrophilic coating is reduced below 15%, more preferably below 10%, and even more preferably below 5% by volume of the atmosphere in contact with the wetted hydrophilic coating.

For present commercial purposes, wetted hydrophilic coatings that are sterilized are preferably present on articles packaged in a gas impermeable packaging. These individually packaged articles are typically medical devices, such as catheters. However, it is possible that the articles are not individually packaged. In such a case, the oxygen in the atmosphere can be reduced by wholly or partially substituting the oxygen in the sterilization chamber with another gas, such as nitrogen, carbon dioxide, argon or another non-reactive gas.

In an embodiment, the oxygen in the atmosphere is reduced by replacing some of the atmosphere in contact with the wetted hydrophilic coating with an alternative gas, such as nitrogen, carbon dioxide, argon or another non-reactive gas. The atmosphere replacement may be performed by simply inserting the alternative gas into a gas impermeable package prior to sealing the gas impermeable package. Inserting the alternative gas at a pressure above atmospheric pressure is desirable, but care should be taken not to insert the alternative gas at too high of pressure or the wetted hydrophilic coating may be affected. For example, some of the wetting agent that has wetted the hydrophilic coating may be inadvertently removed by the high pressure insertion of an alternative gas. Similarly, removal of the oxygen in the atmosphere by a vacuum is also possible, but care should be taken to operate the vacuum to not inadvertently affect the wetted hydrophilic detrimentally. Of course, some gasses other than oxygen may be removed when inserting an alternative gas or using a vacuum, for instance if the original atmosphere is air, but reducing the amount of oxygen in an atmosphere in contact with the wetted hydrophilic coating is achieved if the amount of oxygen is less than prior to carrying out the step.

In an embodiment, the oxygen in the atmosphere is reduced by incorporating an oxygen scavenging packaging component. An oxygen scavenging packaging component may be an item inside a gas impermeable packaging or part of the gas impermeable packaging itself.

Accordingly, in a further embodiment, an oxygen scavenging packaging component is included in the form of an oxygen scavenging packet. For example, the oxygen scavenging packet may be a gas-permeable package containing an oxygen scavenger. The oxygen scavenging packet may be secured or otherwise included inside a gas impermeable packaging. Preferably, such an oxygen scavenging packet is held out of contact with the wetted hydrophilic coating.

The use of such oxygen scavenging packets allows for oxygen scavengers contained within the packet that are not necessarily biocompatible or dissolvable in a wetted hydrophilic coating. For example, the oxygen scavenger in the oxygen scavenging packet may be iron powder, zinc powder, manganese powder, vitamin C, or sodium thiosulfate. Commercial examples of oxygen scavenging packets that are satchets containing an oxygen scavenger are Ageless from Mitsubisihi Gas and Chemical Co., Japan, ATCO products from Emco Packaging Systems, UK, and Standa Industries, France, Freshilizers series from Toppan Printing, Japan, FreshPax® and FreshMax® from Multisorb Technologies, Inc. USA, Bioka oxygen absorbing satchets from Bioka Ltd. Finland, and Oxyguard from Toyo Seikan Kaisha, Japan. In an embodiment, the oxygen scavenging packet is water-activated.

In an embodiment, the oxygen scavenging packaging component is an oxygen scavenging surface. Such oxygen scavenging surfaces are known from, for example U.S. Pat. No. 6,406,766 and U.S. Pat. No. 6,346,308, assigned to BP Corporation of North America, and US20080206500, assigned to DSM IP Assets BV, each hereby incorporated by reference in their entirety. Such an oxygen scavenging surface may be formed from a co-extruded plastic. Oxygen scavenging surfaces are available commercially, for example as Cryovac® OS Films—Active Barrier Films.

Such an oxygen scavenging surface may be present as an internal surface of an outer packaging or as a separate packaging component within an outer packaging. In an embodiment, the oxygen scavenging packaging component is a sleeve comprising an oxygen scavenging surface that is placed around an article inside an outer packaging. Such a sleeve may have the added benefit of providing a surface with which the article may be handled without touching a surface of the article immediately prior to use. In an embodiment, the sleeve is gas impermeable.

In an embodiment of the invention, a method of sterilizing a packaged article is provided comprising the step of sterilizing with radiation a package comprising an article and a gas impermeable packaging enclosing the article, the article comprising a wetted hydrophilic coating and the wetted hydrophilic coating comprising a thiosulfate anion. In a further embodiment, a method of sterilizing a packaged article is provided comprising the step of sterilizing with radiation a package comprising an article and a gas impermeable packaging enclosing the article, the article comprising a wetted hydrophilic coating and the wetted hydrophilic coating comprising an oxygen scavenger comprising a thiosulfate anion, and the package comprising an atmosphere within the gas impermeable packaging and in contact with the wetted hydrophilic coating that has an amount of oxygen that is less than an amount of oxygen that would have been present if oxygen scavengers present in the wetted hydrophilic coating were alone acting on ambient air at the time of packaging within the gas impermeable packaging.

By ambient air at the time of packaging it is meant the composition of the surrounding gasses present at the time of packaging that contain a sufficient amount of oxygen for a human to function normally for an extended period of time without the aid of a breathing apparatus. Ambient air at the time of packaging generally has a percentage of oxygen that is similar to the atmosphere of earth (approximately 20.9% oxygen) at a pressure of 1 atm and may be controlled in some way. For example, ambient air at the time of packaging may be controlled by controlling the temperature and/or humidity of the ambient air at the time of packaging. The situation of packaging an article in an environment comprising an amount of oxygen that is not a sufficient amount of oxygen for a human to function normally for an extended period of time without the aid of a breathing apparatus would not be considered packaging in ambient air, but would rather be a step of reducing the amount of oxygen in an atmosphere in contact with the wetted hydrophilic coating in addition to any reduction in oxygen provided by oxygen scavengers that may be present in the wetted hydrophilic coating.

An embodiment of the invention is a method of packaging an article comprising forming a wetted hydrophilic coating comprising a thiosulfate anion on a surface of an article, and enclosing the article in a gas impermeable packaging.

Another embodiment of the invention is a method of packaging an article comprising forming a wetted hydrophilic coating comprising water and a thiosulfate anion on a surface of an article, and enclosing the article in a gas impermeable packaging. Another embodiment of the invention is a method of packaging an article comprising, providing an article comprising a hydrophilic coating; wetting the hydrophilic coating with a wetting agent comprising a thiosulfate anion; and enclosing the article in a gas impermeable packaging. A further embodiment of the invention is a method of packaging an article comprising, providing an article comprising a hydrophilic coating; wetting the hydrophilic coating with a wetting agent comprising water and a thiosulfate anion; and enclosing the article in a gas impermeable packaging.

A further embodiment of the invention is a method of packaging an article comprising, forming a wetted hydrophilic coating comprising a thiosulfate anion; reducing the amount of oxygen in an atmosphere in contact with the wetted hydrophilic coating in addition to any reduction in oxygen provided by oxygen scavengers present in the wetted hydrophilic coating; and enclosing the wetted hydrophilic coating in a gas impermeable packaging.

An article may be enclosed in a gas impermeable packaging by any number of common methods. For example, the article may be enclosed in gas impermeable packaging by sealing the gas impermeable packaging. For example, the sealing may be carried out by activating an adhesive. Sealing could also be performed by bonding together two surfaces of a gas impermeable packaging with the aid of heat and/or pressure.

Another embodiment of the invention is a package comprising an article comprising a wetted hydrophilic coating, the wetted hydrophilic coating comprising a hydrophilic coating, water, a thiosulfate anion, and a buffer for maintaining the pH at 6 or above, more preferably at 6.5 or above, more preferably at 7 or above; and a gas impermeable packaging enclosing the article. Another embodiment of the invention is a package comprising an article comprising a wetted hydrophilic coating, the wetted hydrophilic coating comprising a hydrophilic coating, water, an oxygen scavenger comprising a thiosulfate anion, and a buffer for maintaining the pH at 6 or above, more preferably at 6.5 or above, more preferably at 7 or above; a gas impermeable packaging enclosing the article; and an atmosphere within the gas impermeable packaging and in contact with the wetted hydrophilic coating that has an amount of oxygen that is less than an amount of oxygen that would have been present if oxygen scavengers present in the wetted hydrophilic coating were alone acting on ambient air at the time of packaging within the gas impermeable packaging. In an embodiment, sterilization is performed by gamma rays or electron beam. In an embodiment, sterilization is performed by gamma rays or electron beam at a dosage of greater than 25 kGy, preferably greater than 30 kGy. Catheters are typically sterilized with a dose of radiation of from 25 to 50 kGy, preferably 25 to 45 kGy.

Additional Description of Certain Preferred Embodiments

Embodiment 101 of the Invention

A wetting agent for wetting a hydrophilic coating comprising a thiosulfate anion, water, and a buffer for maintaining the pH at 6 or above, more preferably at 6.5 or above, more preferably at 7 or above.

Embodiment 102 of the Invention

The wetting agent of Embodiment 101, wherein water is present in an amount of at least 50 wt %, more preferably at least 70 wt %, and more preferably at least 90 wt %, based on the total weight of the wetting agent.

Embodiment 103 of the Invention

The wetting agent of Embodiment 101 or 102, wherein the thiosulfate anion is present in an amount of from 0.05 to 3 wt %, more preferably from 0.1 to 2.5 wt %, more preferably from 0.3 to 2.0 wt %, more preferably from 0.3 to 1.5 wt %, based on the total weight of the wetting agent.

Embodiment 104 of the Invention

The wetting agent of any one of Embodiments 101-103, wherein the pH of the wetting agent is from 6 to 9, more preferably from 6.5 to 9, more preferably from 7 to 9, more preferably from 7 to 8.

Embodiment 105 of the Invention

The wetting agent of any one of Embodiments 101-104, wherein the buffer comprises a water soluble base having a pKb from 5 to 10.

Embodiment 106 of the Invention

The wetting agent of any one of Embodiments 101-105, wherein the buffer capacity is 5 mmol or greater at at least one starting pH of from 6 to 8.5, more preferably from 6 to 8, more preferably from 6.5 to 8, and more preferably from 7 to 8.

Embodiment 107 of the Invention

The wetting agent of any one of Embodiments 101-105, wherein the buffer capacity is from 5 mmol to 500 mmol at at least one starting pH of from 6 to 8.5, more preferably from 6 to 8, more preferably from 6.5 to 8, and more preferably from 7 to 8.

Embodiment 108 of the Invention

The wetting agent of any one of Embodiments 101-105, wherein the buffer capacity is from 5 mmol to 300 mmol at at least one starting pH of from 6 to 8.5, more preferably from 6 to 8, more preferably from 6.5 to 8, and more preferably from 7 to 8.

Embodiment 109 of the Invention

The wetting agent of any one of Embodiments 101-108, wherein the thiosulfate anion is present as sodium thiosulfate, ammonium thiosulfate, barium thiosulfate, calcium thiosulfate, magnesium thiosulfate, potassium thiosulfate, lithium thiosulfate, iron thiosulfate, zinc thiosulfate, tin thiosulfate, silver thiosulfate or hydrates thereof.

Embodiment 110 of the Invention

The wetting agent of any one of Embodiments 101-109, wherein the buffer comprises carbonate, acetate, formate, benzoate, a phosphate buffer, ACES, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, or AMPSO, or salts of any of the foregoing, or combinations of any of the foregoing, preferably a phosphate buffer.

Embodiment 111 of the Invention

The wetting agent of any one of Embodiments 101-110, further comprising from 1 wt % to 20 wt %, more preferably from 2 wt % to 10 wt %, more preferably from 4 wt % to 10 wt %, based on the total amount of wetting agent, of a component selected from the group consisting of glycerol, glycerol esters, glycerol ethers, glycols, glycolesters and glycolethers, preferably a component selected from the group consisting of glycerol, monoacetin, diacetin, diacetone alcohol, diethyleneglycol, triethyleneglycol, tetraethyleneglycol, propyleneglycol and dipropyleneglycol.

Embodiment 112 of the Invention

The wetting agent of any one of Embodiments 101-111, further comprising a further radical scavenger Embodiment 113 of the Invention The wetting agent of any one of Embodiments 101-112, further comprising a preservative.

Embodiment 114 of the Invention

The wetting agent of any one of Embodiments 101-113, further comprising a water soluble polymer.

Embodiment 115 of the Invention

The wetting agent of any one of Embodiments 101-110, wherein the wetting agent consists essentially of a thiosulfate anion, water, and a buffer for maintaining the pH at 6 or above, more preferably at 6.5 or above, more preferably at 7 or above.

Embodiment 116 of the Invention

The wetting agent of any one of Embodiments 101-110, wherein the wetting agent consists of a thiosulfate anion, water, and a buffer for maintaining the pH at 6 or above, more preferably at 6.5 or above, more preferably at 7 or above.

Embodiment 117 of the Invention

The wetting agent of Embodiment 111, wherein the wetting agent consists essentially of a thiosulfate anion, water, a buffer for maintaining the pH at 6 or above, more preferably at 6.5 or above, more preferably at 7 or above, and a component selected from the group consisting of glycerol, glycerol esters, glycerol ethers, glycols, glycolesters and glycolethers, preferably a component selected from the group consisting of glycerol, monoacetin, diacetin, diacetone alcohol, diethyleneglycol, triethyleneglycol, tetraethyleneglycol, propyleneglycol and dipropyleneglycol.

Embodiment 118 of the Invention

The wetting agent of Embodiment 111, wherein the wetting agent consists of a thiosulfate anion, water, and a buffer for maintaining the pH at 6 or above, more preferably at 6.5 or above, more preferably at 7 or above, and a component selected from the group consisting of glycerol, glycerol esters, glycerol ethers, glycols, glycolesters and glycolethers, preferably a component selected from the group consisting of glycerol, monoacetin, diacetin, diacetone alcohol, diethyleneglycol, triethyleneglycol, tetraethyleneglycol, propyleneglycol and dipropyleneglycol.

Embodiment 119 of the Invention

An article, preferably a medical device, comprising a wetted hydrophilic coating wetted with the wetting agent of any one of Embodiments 101-118.

Embodiment 120 of the Invention

The article of Embodiment 119, wherein the wetted hydrophilic coating comprises a hydrophilic coating that is formed by curing a hydrophilic coating composition, the hydrophilic coating composition comprising at least 70 wt %, preferably at least 80 wt %, more preferably at least 90 wt % of hydrophilic polymer, based on the total dry weight of the hydrophilic coating composition.

Embodiment 121 of the Invention

A package comprising the article of Embodiment 119 or 120, wherein the package preferably further comprises a gas impermeable packaging enclosing the article, and wherein the package is preferably sterilized by radiation.

Embodiment 122 of the Invention

The package of Embodiment 121, further comprising an oxygen scavenging packaging component.

Embodiment 123 of the Invention

The package of Embodiment 121 or 122, wherein the package comprises a gas impermeable packaging enclosing the article and comprises an atmosphere within the gas impermeable packaging and in contact with the wetted hydrophilic coating that has an amount of oxygen that is less than an amount of oxygen that would have been present if oxygen scavengers present in the wetted hydrophilic coating were alone acting on ambient air at the time of packaging within the gas impermeable packaging.

Embodiment 201 of the Invention

A wetted hydrophilic coating comprising a hydrophilic coating, a thiosulfate anion, water, and a buffer for maintaining the pH at 6 or above, more preferably at 6.5 or above, more preferably at 7 or above.

Embodiment 202 of the Invention

The wetted hydrophilic coating of Embodiment 201, wherein water is present in an amount of at least 50 wt %, more preferably at least 70 wt %, and more preferably at least 90 wt %, based on the total weight of the wetted hydrophilic coating.

Embodiment 203 of the Invention

The wetted hydrophilic coating of Embodiment 201 or 202, wherein the thiosulfate anion is present in an amount of from 0.05 to 3 wt %, more preferably from 0.1 to 2.5 wt %, more preferably from 0.3 to 2.0 wt %, more preferably from 0.3 to 1.5 wt %, based on the total weight of the wetted hydrophilic coating.

Embodiment 204 of the Invention

The wetted hydrophilic coating of any one of Embodiments 201-203, wherein the pH of the wetted hydrophilic coating is from 6 to 9, more preferably from 6.5 to 9, more preferably from 7 to 9, more preferably from 7 to 8.

Embodiment 205 of the Invention

The wetted hydrophilic coating of any one of Embodiments 201-204, wherein the buffer comprises a water soluble base having a pKb from 5 to 10.

Embodiment 206 of the Invention

The wetted hydrophilic coating of any one of Embodiments 201-205, wherein the buffer capacity is 5 mmol or greater at at least one starting pH of from 6 to 8.5, more preferably from 6 to 8, more preferably from 6.5 to 8, and more preferably from 7 to 8.

Embodiment 207 of the Invention

The wetted hydrophilic coating of any one of Embodiments 201-205, wherein the buffer capacity is from 5 mmol to 500 mmol at at least one starting pH of from 6 to 8.5, more preferably from 6 to 8, more preferably from 6.5 to 8, and more preferably from 7 to 8.

Embodiment 208 of the Invention

The wetted hydrophilic coating of any one of Embodiments 201-205, wherein the buffer capacity is from 5 mmol to 300 mmol at at least one starting pH of from 6 to 8.5, more preferably from 6 to 8, more preferably from 6.5 to 8, and more preferably from 7 to 8.

Embodiment 209 of the Invention

The wetted hydrophilic coating of any one of Embodiments 201-208, wherein the buffer comprises carbonate, acetate, formate, benzoate, a phosphate buffer, ACES, PIPES, MOPSO, Bis-Tris Propane, BES, MOPS, TES, HEPES, DIPSO, MOBS, TAPSO, Trizma, HEPPSO, POPSO, TEA, EPPS, Tricine, Gly-Gly, Bicine, HEPBS, TAPS, AMPD, TABS, or AMPSO, or salts of any of the foregoing, or combinations of any of the foregoing, preferably a phosphate buffer.

Embodiment 210 of the Invention

The wetted hydrophilic coating of any one of Embodiments 201-209, further comprising from 1 wt % to 20 wt %, more preferably from 2 wt % to 10 wt %, more preferably from 4 wt % to 10 wt %, based on the total amount of wetted hydrophilic coating, of a component selected from the group consisting of glycerol, glycerol esters, glycerol ethers, glycols, glycolesters and glycolethers, preferably a component selected from the group consisting of glycerol, monoacetin, diacetin, diacetone alcohol, diethyleneglycol, triethyleneglycol, tetraethyleneglycol, propyleneglycol and dipropyleneglycol.

Embodiment 211 of the Invention

The wetted hydrophilic coating of any one of Embodiments 201-210, further comprising a further radical scavenger

Embodiment 212 of the Invention

The wetted hydrophilic coating of any one of Embodiments 201-211, further comprising a preservative.

Embodiment 213 of the Invention

The wetted hydrophilic coating of any one of Embodiments 201-212, wherein the thiosulfate anion is present as sodium thiosulfate, ammonium thiosulfate, barium thiosulfate, calcium thiosulfate, magnesium thiosulfate, potassium thiosulfate, lithium thiosulfate, iron thiosulfate, tin thiosulfate, silver thiosulfate or hydrates thereof.

Embodiment 214 of the Invention

The wetted hydrophilic coating of any one of embodiments 201-213, wherein the hydrophilic coating is formed by curing a hydrophilic coating composition, the hydrophilic coating composition comprising at least 70 wt %, preferably at least 80 wt %, more preferably at least 90 wt % of hydrophilic polymer, based on the total dry weight of the hydrophilic coating composition.

Embodiment 215 of the Invention

An article, preferably a medical device, comprising the wetted hydrophilic coating of any one of Embodiments 201-214.

Embodiment 216 of the Invention

A package comprising the article of Embodiment 215, wherein the package preferably further comprises a gas impermeable packaging enclosing the article, and wherein the package is preferably sterilized by radiation.

Embodiment 217 of the Invention

The package of Embodiment 216, further comprising an oxygen scavenging packaging component.

Embodiment 218 of the Invention

The package of Embodiment 216 or 217, wherein the package comprises a gas impermeable packaging enclosing the article and comprises an atmosphere within the gas impermeable packaging and in contact with the wetted hydrophilic coating that has an amount of oxygen that is less than an amount of oxygen that would have been present if oxygen scavengers present in the wetted hydrophilic coating were alone acting on ambient air at the time of packaging within the gas impermeable packaging.

Embodiment 301 of the Invention

A method of reducing the deterioration of a wetted hydrophilic coating comprising water and subjected to sterilization by radiation comprising the step of incorporating in the wetted hydrophilic coating a thiosulfate anion and a buffer for maintaining the pH at 6 or above, more preferably at 6.5 or above, more preferably at 7 or above.

Embodiment 302 of the Invention

The method of Embodiment 301 of the invention, wherein the step of incorporating a thiosulfate anion is preferably performed by incorporating a compound selected from the group consisting of sodium thiosulfate, ammonium thiosulfate, barium thiosulfate, calcium thiosulfate, magnesium thiosulfate, potassium thiosulfate, lithium thiosulfate, iron thiosulfate, zinc thiosulfate, tin thiosulfate, silver thiosulfate or hydrates thereof into the wetted hydrophilic coating.

Embodiment 303 of the Invention

The method of Embodiment 301 or 302 of the invention, further comprising the step of reducing the amount of oxygen in an atmosphere in contact with the wetted hydrophilic coating in addition to any reduction in oxygen provided by oxygen scavengers present in the wetted hydrophilic coating.

Embodiment 401 of the Invention

A method of sterilizing a packaged article comprising the step of sterilizing with radiation the article of any one of Embodiments 119, 120 or 215, or the package of any one of Embodiments 121-123 or 216-218.

Embodiment 402 of the Invention

A method of packaging an article comprising enclosing the article of any one of Embodiments 119, 120 or 215, in a gas impermeable packaging.

The following examples are used to further illustrate the invention, but, of course, should not be construed as in any way limiting its scope.

EXAMPLES

Experiment 1

Characterization of Deterioration

Hydrophilic coatings are provided on pieces of 14 Fr PVC tubing with a length of 40 cm. The tubing is useful for intermittent catheter products.

Coating and Curing Process

The primer composition was P41001, a primer composition available from DSM Biomedical, Inc. P41001 comprises a hydrophilic polymer comprising reactive groups, a further hydrophilic polymer, a photoinitiator and greater than 90 wt % of solvent, based on the total weight of the primer composition. The hydrophilic coating composition was TC43005, a UV-curable hydrophilic coating composition available from DSM Biomedical, Inc. TC43005 comprises a hydrophilic polymer, a polyelectrolyte hydrophilic polymer, a photoinitiator, and greater than 90 wt % of solvent, based on the total weight of the hydrophilic coating composition.

A metal mandrel was inserted into the end of a piece of PVC tubing and subsequently attached into the device holder of a Harland PCX coater. The dip length for the primer composition was 35 cm. The dip length for the hydrophilic coating composition was 34 cm.

Pieces of PVC tubing were dip coated and cured using the Harland PCX coater. Extraction speed of the coated tubing was 1 cm/s for both the primer and hydrophilic coating formation. Cure took place directly after application of the hydrophilic coating composition. Intensity of the lamps was on average 60 mW/cm2 and was measured using a Harland UVR 335 (also known as IL 1400), equipped with an International Light detector SED 005#989. Input optic: W#11521, filter wbs320#27794. The instruction manual of International Light was applied, which is available on the internet: www.intl-light.com. UV dose was approximately 0.9 J/cm2 for the primer and 21.6 J/cm2 for the hydrophilic coating. The primer composition was coated and cured first, and then the hydrophilic coating composition was coated and cured. After curing, a coated tubing comprising a hydrophilic coating was obtained.

Preparation of a Wetted Hydrophilic Coating

A wetting agent is formed by weighing the components of the wetting agent and simply mixing together the components in a glass bottle. The compositions of the wetting agents are shown in the below Table 3 in weight percent, based on the total amount of wetting agent. All components other than water were obtained from Sigma Aldrich. The water was demineralized water. Shortly after preparing the wetting agent, the hydrophilic coatings on the pieces of coated tubing formed above are wetted by immersion for one minute in the wetting agent, thereby forming pieces of coated tubing comprising a wetted hydrophilic coating.

Packaging

A gas impermeable, heat sealable packaging with an external surface of an aluminum foil and an internal surface of polyethylene foil were obtained from Steripack (U/P Pouch 70*505 mm SO5198). 2.5 ml of wetting agent was inserted into each gas impermeable packaging prior to placing the coated tubing comprising a wetted hydrophilic coating in the gas impermeable packaging. Each piece of coated tubing comprising a wetted hydrophilic coating was then individually placed in a gas impermeable package and the package was sealed by applying heat, thereby forming a package.

Sterilization

The packages were sterilized in the wetting fluid by exposing them to 45+/−5 kGy of γ-radiation.

Lubricity, Durability and Dry-Out Time

After sterilization, the pieces of coated tubing comprising a wetted hydrophilic coating are tested for lubricity, durability, and dry-out time. The sterilized package was opened shortly before testing. The tests were performed using a Harland FTS5000 Friction Tester (HFT). The lubricity and durability measurements are performed in water, whereas dry-out time measurements are performed in air. The protocol was as indicated in the following table:

TABLE 1

| HFT settings | |
| --- | --- |
| transport movement (cm) | 10 |
| clamp force (g) | 300 |
| pull speed (cm/s) | 1 |
| acceleration time (sec) | 2 |
| number of rubs | 25 |

Friction tester pads from Harland Medical Systems were used: P/N 102692, FTS5000 Friction Tester Pads, 0.125"0.5"0.125"60 durometer. A metal mandrel was inserted into a piece of coated tubing comprising a wetted hydrophilic coating and the test started.

The lubricity of the wetted hydrophilic coating is defined as the friction force measured after the first cycle. A lubricity (friction force) of less than 15 gram is considered to be acceptable. The durability of the wetted hydrophilic coating is defined as the difference between the friction force measured after the $25^{th}$ cycle and the friction force measured after the first cycle. The durability is a measure of the adhesion of the wetted hydrophilic coating on a surface and coating integrity. A durability of less than 5 grams is considered to be very good.

A typical lubricity value for unsterilized coated tubing with a wetted hydrophilic coating wetted with 100% water is 5-10 grams. A typical value for durability of such unsterilized coated tubing is less than 5 gram.

Dry-out time was determined by measuring the friction in gram as a function of time the coated tubing comprising a wetted hydrophilic coating had been exposed to air on the HFT (see above). Relative humidity during the measurement was kept between 45-55% and the temperature between 19 and 22° C. Measurements were performed after 5 minutes after taking the coated tubing out of the package. The machine settings are the same as in Table 1, but with the clamp-force set at 100 g. If friction measured after 5 minutes is less than 10 grams, then the dry-out time is greater than 5 minutes. If friction is immediately higher than 10 grams, on account of deterioration of the wetted hydrophilic coating, then no dry-out time could be observed. A typical value for dry-out time of unsterilized coated tubing with a wetted hydrophilic coating wetted with 100% water is a 5 minutes or greater.

Characterization of Deterioration

Deterioration is characterized by loss of lubricity and durability in the friction tester. The amount of deterioration is also assessed by comparison to the lubricity of an unsterilized wetted hydrophilic coating with 100 wt % water as the wetting agent by gentle rubbing of the wetted coated tubing between the pointer finger and the thumb immediately after removal from the sterilized package. Deterioration of the wetted hydrophilic coating was assessed using the criteria in Table 2, below.

TABLE 2

| Deterioration Level | Description |
| --- | --- |
| 0 | No deterioration observed |
| 1 | Deterioration is observed, but the lubricity is not significantly affected. Thinning of the wetted hydrophilic coating is observed. |
| 2 | Deterioration is observed and the lubricity of the wetted hydrophilic coating is somewhat adversely affected. |
| 3 | Significant improvement over a wetting agent comprising 100 wt % of water, but significant deterioration is still observed. |
| 4 | Very little improvement over a wetting agent comprising 100 wt % of water, significant deterioration is observed. |
| 5 | Baseline level of deterioration for the case when the wetting agent comprises 100 wt % water. |

The pre-sterilization lubricity of each sample was about 5 to 10 g. Each wetted hydrophilic coating was tested in triplicate, except for Examples 9, 10, and 15, which were tested in quintuplicate. The reported value is an average. Results of the experiment are reported in Table 3a and Table 3b below.

TABLE 3a

Experiment 1 Results

| Ex. | Wetting agent | Lubricity (g) | Durability (g) | Dry-out time (min.) | Deterioration level |
|---|---|---|---|---|---|
| 1 | 100 wt % water | >100 | >100 gr after 2$^{nd}$ cycle | No dry-out time | 5 |
| 2 | 99 wt % water + 1 wt % vitamin C | >100 | >100 after 2$^{nd}$ cycle | No dry-out time | 5 |
| 3 | 98.5 wt % water + 1.5 wt % vitamin C | >100 | >100 after 2$^{nd}$ cycle | No dry-out time | 5 |
| 4 | 99 wt % water + 1 wt % sodium sulfite | >100 | >100 after 2$^{nd}$ cycle | No dry-out time | 5 |
| 5 | 99 wt % water + 1 wt % sodium metabisulfite | >100 | >100 after 2$^{nd}$ cycle | No dry-out time | 5 |
| 6 | 98 wt % water + 2 wt % cysteine | >100 | >100 after 2$^{nd}$ cycle | No dry-out time | 5 |
| 7 | 70 wt % water + 30 wt % glycerol | >100 | >100 after 2$^{nd}$ cycle | No dry-out time | 5 |
| 8 | 70 wt % water + 30 wt % propylene glycol | >100 | >100 after 2$^{nd}$ cycle | No dry-out time | 5 |
| 9 | 1 wt % niacinamide, 5 wt % propylene glycol, 94 wt % water | 22 | >100 after 5$^{th}$ cycle | Not Tested | 4 |

TABLE 3b

Experiment 1 Results (cont.)

| Ex. | Wetting agent | Lubricity (g) | Durability (g) | Dry-out time (min.) | Deterioration level |
|---|---|---|---|---|---|
| 10 | 1 wt % sodium salicylate, 5 wt % propylene glycol, 94 wt % water | 6 | See below | Not Tested | 3 |
| 11 | 99 wt % water + 1 wt % sodium thiosulfate | 6 | 0 | >5 | 0 |
| 12 | 98.5 wt % water + 1.5 wt % sodium thiosulfate | 6 | 0 | >5 | 0 |
| 13 | 97.3 wt % water + 1.5 wt % sodium thiosulfate + 1 wt % sodium carbonate + 0.2 wt % methyl paraben | 5 | 0 | >5 | 1 |
| 14 | 94 wt % water + 5 wt % propylene glycol + 1 wt % sodium thiosulfate | 6 | 0 | Not Tested | 0 |
| 15 | 93.809 wt % water + 5 wt % propylene glycol + 1 wt % sodium thiosulfate + 0.065 wt % sodium phosphate monobasic monohydrate + 0.126 wt % sodium phosphate di basic heptahydrate | 6 | 0 | >5 | 0 |

Discussion of Experiment 1 Results

A lubricity (friction force) of less than 15 gram is considered to be acceptable. A durability of less than 5 grams is considered to be very good. A lubricity or durability of >100 indicates complete deterioration of the wetted hydrophilic coating during the test. For durability testing, complete wetted hydrophilic coating deterioration may have occurred at any point during the 25 cycles. After sterilization the wetted hydrophilic coating wetted entirely with water deteriorated completely. The addition of vitamin C, a radical and/or oxygen scavenger, shows no significant improvement. Similar results are obtained with various other components. Although a lubricity value for the wetted hydrophilic coatings wetted with a niacinamide containing composition was obtained, the wetted hydrophilic coating quickly deteriorated in durability testing. The wetted hydrophilic coatings wetted with the sodium salicylate containing composition produced very good initial lubricity data in all samples. Of the five sodium salicylate containing samples tested, four showed durability values of 0, while one failed after the r cycle on one section of the wetted hydrophilic coating and after the 14$^{th}$ cycle on another section of the wetted hydrophilic coating, which indicates substantial deterioration of the wetted hydrophilic coating. Additionally, the presence of sodium salicylate in a wetted hydrophilic coating is usually undesirable because sodium salicylate is a drug and it is preferred that only components that are not pharmaceutically active are present in the wetted hydrophilic coating. In all experiments wherein the wetting agent contained sodium thiosulfate the wetted hydrophilic coating performance was substantially maintained after sterilization.

Experiment 2

Impact of Buffer on Wetting Agent Stability

Two wetting agent compositions comprising a thiosulfate anion were prepared: one with a buffer and one without. The two wetting agent compositions are shown in Table 4 and Table 5.

TABLE 4

Unbuffered Wetting Agent Composition used in Experiment 2

| Component | Amount (wt. %) |
|---|---|
| water | 94 |
| sodium thiosulfate | 1 |
| propylene glycol | 5 |

TABLE 5

Buffered (0.01M) Wetting Agent Composition used in Experiment 2

| Component | Amount (wt. %) |
|---|---|
| water | 93.809 |
| sodium thiosulfate | 1.000 |
| propylene glycol | 5.000 |
| sodium phosphate mono basic monohydrate | 0.065 |
| sodium phosphate di basic heptahydrate | 0.126 |

The two wetting agents compositions were stored at 70° C. for five weeks. After five weeks the amount of decomposition of the thiosulfate anion was determined by means of ion chromatography with suppressed conductivity as detection mode. The samples are diluted with eluent about 2000 times. The equipment used was a Thermo Fisher ion chromatograph DX 500 with conductivity detection; suppressor: Thermo Fisher ASRS-300, 4 mm; column: Thermofisher IonPac AG16 (50×4 mm)+IonPac AG16 (250×4 mm); eluent: 17.5 mM NaOH; flow: 1 ml/min; column temperature: 30° C.; autosampler: Agilent 1200 series; injection volume: 10 µl.

The unbuffered wetting agent composition was 15% decomposed while the buffered wetting agent composition was only 7% decomposed, indicating significantly improved stability of the thiosulfate anion in the buffered wetting agent composition.

Experiment 3

Effect of Buffering and pH on Wetting Agent Stability

Two wetting agent compositions comprising a thiosulfate anion were prepared. The wetting compositions were identical except for a differing concentration of buffer. In each case, the buffer consisted of sodium phosphate mono basic monohydrate and sodium phosphate di basic heptahydrate. The compositions are detailed in Tables 6 and 7 below.

TABLE 6

0.01M Buffer Wetting Agent Composition used in Experiment 3

| Component | Amount (wt. %) |
| --- | --- |
| water | 93.809 |
| sodium thiosulfate | 1.000 |
| propylene glycol | 5.000 |
| sodium phosphate mono basic monohydrate | 0.065 |
| sodium phosphate di basic heptahydrate | 0.126 |

TABLE 7

0.1M Buffer Wetting Agent Composition used in Experiment 3

| Component | Amount (wt. %) |
| --- | --- |
| water | 92.09 |
| sodium thiosulfate | 1.00 wt % |
| propylene glycol | 5.00 |
| sodium phosphate mono basic monohydrate | 0.65 |
| sodium phosphate di basic heptahydrate | 1.26 |

After preparation, the compositions were adjusted to pH 6, 7, 8, 9, or 10, as specified, by addition of HCl or NaOH solution. The various compositions were stored at 50° C. for up to 12 weeks. A visual and smell test was performed on each sample 2 weeks, 3 weeks, 7 weeks, and 12 weeks after preparation and storage. The results of the Experiment are shown in Table 8.

TABLE 8

Results of Experiment 3

| Ex. | Buffer | pH | 2 weeks visual | 2 weeks smell | 3 weeks visual | 3 weeks smell | 7 weeks visual | 7 weeks smell | 12 weeks visual | 12 weeks smell |
| --- | --- | --- | --- | --- | --- | --- | --- | --- | --- | --- |
| 1 | 0.01M | 6 | clear | sulfury | clear | sulfury | clear | sulfury | clear | sulfury |
| 2 | 0.01M | 7 | clear | neutral | clear | neutral | clear | neutral | clear | neutral |
| 3 | 0.01M | 8 | clear | neutral | clear | neutral | turbid | neutral | turbid | neutral |
| 4 | 0.01M | 9 | clear | neutral | turbid | neutral | turbid | neutral | turbid | neutral |
| 5 | 0.01M | 10 | turbid | neutral | turbid | neutral | turbid | neutral | turbid | neutral |
| 6 | 0.1M | 6 | clear | sulfury | clear | sulfury | clear | neutral | clear | sulfury |
| 7 | 0.1M | 7 | clear | neutral | clear | neutral | clear | Slight "off" smell | clear | Slight "off" smell |
| 8 | 0.1M | 8 | clear | neutral | clear | neutral | turbid | neutral | turbid | neutral |
| 9 | 0.1M | 9 | turbid | neutral | turbid | neutral | turbid | neutral | turbid | neutral |
| 10 | 0.1M | 10 | turbid | neutral | turbid | neutral | turbid | neutral | turbid | neutral |

Discussion of Experiment 3 Results

In addition to the examples reported above, a wetting agent sample according to the formulation of Table 6 at a pH of 5 for 1 week at 50° C. exhibits a continued sulfury smell. An initial sulfury smell is present in all examples. However, it was found that this sulfury smell disappears within one week of storage at 50° C. for the examples at pH 7 or above. In contrast, the smell does not dissipate significantly for the samples having a pH of 5 or 6. This indicates continued instability of the thiosulfate anion at a pH of 6 or below. The stability is improves at a pH of greater than 6 and less than 10, especially at a pH of from 7 to 9, and best at a pH of from 7 to 8.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain embodiments detail certain optional features as further embodiments of the invention, the description is meant to encompass and specifically disclose all combinations of these features unless specifically indicated otherwise or physically impossible.

The invention claimed is:

1. A method of sterilizing a packaged article comprising the step of sterilizing with radiation a gas impermeable package enclosing an article comprising a wetted hydrophilic coating, the wetted hydrophilic coating comprising a hydrophilic coating, a thiosulfate anion, water, and a buffer for maintaining the pH at 7 or above.

2. The method according to claim 1, wherein the wetted hydrophilic coating comprises water in an amount of at least 70 wt %, based on the total weight of the wetted hydrophilic coating and the thiosulfate anion is present in an amount of from 0.05 to 3 wt %, based on the total weight of the wetted hydrophilic coating.

3. The method according to claim 1, wherein the wetted hydrophilic coating comprises water in an amount of at least 90 wt %, based on the total weight of the wetted hydrophilic coating and the thiosulfate anion is present in an amount of from 0.3 to 2 wt %, based on the total weight of the wetted hydrophilic coating.

4. The method according to claim 1, wherein the buffer maintains the pH at from 7 to 9.

5. The method according to claim 1, wherein the pH of the wetted hydrophilic coating is from 7 to 9.

6. The method according to claim 5, wherein the buffer comprises a water soluble base having a pKb of from 5 to 10.

7. The method according to claim 5, wherein the buffer capacity is 5 mmol or greater at at least one starting pH of from 7 to 8.5.

8. The method according to claim 7, wherein the buffer capacity is 5 mmol or greater at at least one starting pH of from 7 to 8.5.

9. The method according to claim 5, wherein the buffer capacity is from 5 mmol to 300 mmol at at least one starting pH of from 7 to 8.5.

10. The method according to claim 5, wherein the buffer is a phosphate buffer.

11. The method according to claim 5, wherein the wetted hydrophilic coating further comprises from 1 wt % to 20 wt %, based on the total amount of wetted hydrophilic coating, of a component selected from the group consisting of glycerol, monoacetin, diacetin, diacetone alcohol, diethyleneglycol, triethyleneglycol, tetraethyleneglycol, propyleneglycol and dipropyleneglycol.

12. The method according to claim 5, wherein the wetted hydrophilic coating further comprises a further radical scavenger.

13. The method according to claim 5, wherein the wetted hydrophilic coating further comprises a preservative.

14. The method according to claim 5, wherein the thiosulfate anion is present as sodium thiosulfate, ammonium thiosulfate, barium thiosulfate, calcium thiosulfate, magnesium thiosulfate, potassium thiosulfate, lithium thiosulfate, iron thiosulfate, zinc thiosulfate, tin thiosulfate, silver thiosulfate or hydrates thereof.

15. The method according to claim 5, wherein the hydrophilic coating is formed by curing a hydrophilic coating composition, the hydrophilic coating composition comprising at least 80 wt % of hydrophilic polymer, based on the total dry weight of the hydrophilic coating composition.

16. The method according to claim 5, wherein the gas impermeable package encloses an oxygen scavenging packaging component.

17. The method according to claim 5, wherein the gas impermeable package comprises an atmosphere within the gas impermeable package and in contact with the wetted hydrophilic coating that has an amount of oxygen that is less than an amount of oxygen that would have been present if oxygen scavengers present in the wetted hydrophilic coating were alone acting on ambient air at the time of packaging within the gas impermeable package.

18. The method according to claim 5, wherein the radiation is gamma rays or electon beam at a dosage of greater than 25 kGy.

19. A sterilized packaged article formed by the method of claim 6.

20. A sterilized packaged article formed by the method of claim 15.

* * * * *